(12) United States Patent
Reddy

(10) Patent No.: US 8,535,906 B2
(45) Date of Patent: Sep. 17, 2013

(54) BIOFUEL MANUFACTURING METHODS AND SYSTEMS INCORPORATING RADIOCARBON ANALYSIS TECHNIQUES

(75) Inventor: Christopher M. Reddy, Falmouth, MA (US)

(73) Assignee: Woods Hole Oceanographic Institution, Woods Hole, MA (US)

( * ) Notice: Subject to any disclaimer, the term of this patent is extended or adjusted under 35 U.S.C. 154(b) by 414 days.

(21) Appl. No.: 12/768,049

(22) Filed: Apr. 27, 2010

(65) Prior Publication Data

US 2010/0273210 A1  Oct. 28, 2010

Related U.S. Application Data

(60) Provisional application No. 61/172,900, filed on Apr. 27, 2009.

(51) Int. Cl.
*C12P 1/00* (2006.01)

(52) U.S. Cl.
USPC .......................................................... 435/41

(58) Field of Classification Search
None
See application file for complete search history.

(56) References Cited

U.S. PATENT DOCUMENTS

| 2009/0087890 A1 | 4/2009 | Pyle et al. |
| 2009/0215137 A1 | 8/2009 | Hawkins et al. |
| 2009/0226990 A1 | 9/2009 | Hawkins et al. |

FOREIGN PATENT DOCUMENTS

WO  WO-2009036087 A1  3/2009

*Primary Examiner* — James Martinell
(74) *Attorney, Agent, or Firm* — Ropes & Gray LLP

(57) ABSTRACT

The systems and methods described herein are directed toward the use of radiocarbon analysis techniques in the manufacture of biofuel products. Among other things, methods and systems for using measured fossil-fuel-derived carbon content in biofuel products to guide the design and modification of biofuel manufacturing systems are disclosed.

10 Claims, 4 Drawing Sheets

BIOFUEL MANUFACTURING METHODS AND SYSTEMS INCORPORATING RADIOCARBON ANALYSIS TECHNIQUES

CROSS-REFERENCE TO RELATED APPLICATION

This application claims the benefit of and incorporates by reference the entire disclosure of U.S. Provisional Patent Application No. 61/172,900 filed on Apr. 27, 2009.

FIELD OF THE INVENTION

This invention relates to biofuel manufacturing processes, and more specifically to regulate the growth of organisms capable of producing a biofuel product via radiocarbon content monitoring.

BACKGROUND OF THE INVENTION

Biofuels and other renewable fossil fuel substitutes are attracting great interest, due to concerns about future availability of fossil fuels. In addition, concerns about climate change have sparked interest in schemes to reduce the emission of carbon into the atmosphere. One potential way to address these problems is to inject carbon into biofuel manufacturing processes in order to capture the carbon. However, biological uptake of carbon materials injected into biofuel manufacturing plants is not well understood. Accordingly, there is a need for improved methods and systems for utilizing carbon emissions in biofuel manufacturing processes.

SUMMARY

The systems and methods described herein are directed toward the use of radiocarbon analysis techniques in the manufacture of biofuel products. Among other things, methods and systems for using measured percentages of fossil-fuel-derived carbon in algae or their biofuel products to guide the design and modification of biofuel manufacturing systems are disclosed.

According to certain aspects of the invention, a method of and system for growing photosynthetic organisms with controlled fossil carbon content for generating a biofuel product are provided. The photosynthetic organisms are disposed within a biofuel growth system configured to receive one or more feedstocks and generate a biofuel product. The feedstock(s) are added to the biofuel growth system, and the fossil carbon content of the biofuel product is measured. A parameter of the feedstock(s) and/or the growth system is regulated based on the measured fossil carbon content.

In some embodiments, the measurement of fossil carbon content may be based on radiocarbon analysis. In one embodiment, the fossil carbon content of the feedstock(s) and/or the fossil carbon content within the biofuel growth system may also be measured, and the regulation of the parameter of the feedstock(s) and/or the growth system may further be based on the measured fossil carbon content of the feedstock(s) and/or the measured fossil carbon content of the growth system. In certain embodiments, the biofuel product may be an intermediate biofuel product or a final biofuel product. Optionally, the feedstock(s) may include a carbon-bearing gas, and the regulation of the parameter of the feedstock(s) and/or the growth system may include adjusting one or more parameter(s) associated with the addition of the carbon-bearing gas to the growth system. In some embodiments, the one or more parameter(s) may include a gas addition rate, a gas addition location, a quantity of gas, a type of gas, and/or a source of gas. The carbon-bearing gas may be a flue gas resulting from the combustion of a fossil fuel, and may be received from a fossil fuel power plant. In some embodiments, the photosynthetic organisms include algae.

BRIEF DESCRIPTION OF THE FIGURES

The foregoing and other objects and advantaged of the invention will be appreciated more fully from the following description thereof, with reference to the accompanying drawings wherein.

DETAILED DESCRIPTION

Figure 1:
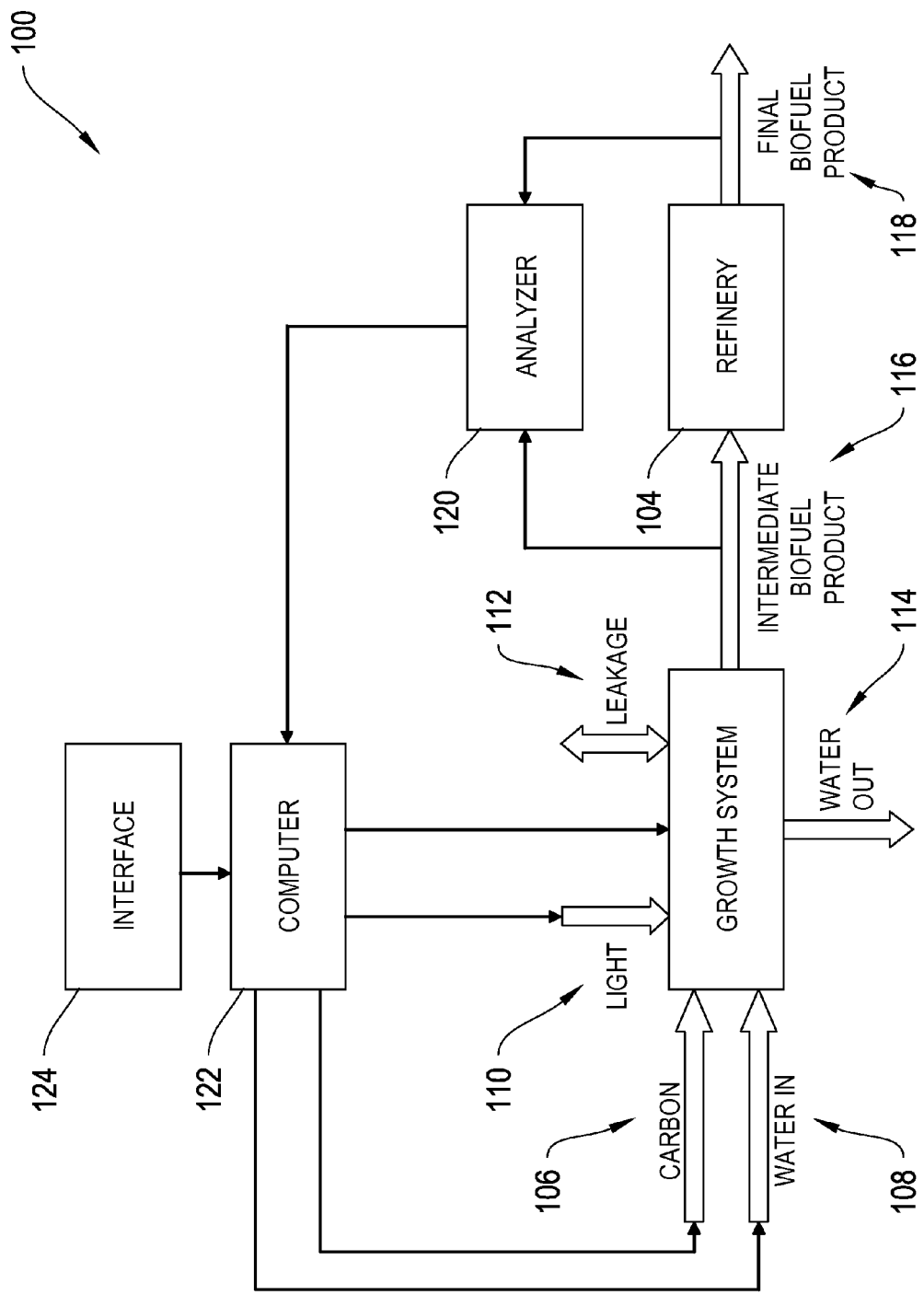
FIG. 1 depicts a system for manufacturing biofuel, according to an illustrative embodiment of the invention.

To provide an overall understanding of the invention, certain illustrative embodiments will now be described, including a system for controlling biofuel manufacture via radiocarbon content monitoring. However, it will be understood by one of ordinary skill in the art that the systems and methods described herein may be adapted and modified for other suitable applications and that such other additions and modifications will not depart from the scope thereof.

Radiocarbon, also known as $^{14}C$, is a radioactive isotope of carbon that is continually generated due to the impact of radiation on carbon-containing gases in the atmosphere. Radiocarbon has a half-life of 5,730 years, and in organic material will decay to undetectable levels after about ten half-lifes, or approximately 58,000 to 62,000 years. Fossil fuels such as coal, oil, or natural gas, because they are produced from organic material that are millions of years old, contain no radiocarbon. In contrast, plants that have been recently grown in ambient atmosphere will generally contain radiocarbon in direct proportion to the amount of radiocarbon in the atmosphere during the time of growth. Hence, biofuel products derived from plants exposed to ambient atmosphere will contain radiocarbon in proportion to the amount of exposure to ambient atmosphere experienced by the plants used to produce the biofuel products. Similarly, if a biofuel product is entirely derived from fossil-fuel-based carbon, such as from plants grown without exposure to ambient atmosphere and only exposed to fossil-fuel-based carbon, it will contain no radiocarbon.

In certain embodiments, a radiocarbon analysis technique may be used to determine the percentage of radiocarbon in a given biofuel sample. In one embodiment, a sample of biofuel may be combusted to provide carbon dioxide gas. This carbon dioxide gas may be collected and converted into a solid form of carbon, such as graphite. The solid carbon sample may be analyzed by, for example, accelerator mass spectrometry (AMS) methods which separates the carbon isotopes in the solid carbon sample, such as those shown in "Determination of Biodiesel Blending Percentages Using Natural Abundance Radiocarbon Analysis: Testing the Accuracy of Retail Biodiesel Blends," Reddy et al., Environ. Sci. Technol. (2008), hereby incorporated by reference in its entirety. Thus, the number of radiocarbons may be counted and compared to the total amount of carbon in the sample to derive a ratio of radiocarbon to stable, non-radioactive carbon. In other embodiments, any radiocarbon measurement techniques may be used, including, but not limited to, beta decay, and intracavity optogalvanic spectroscopic methods such that those shown in "Intracavity Optogalvanic Spectroscopy, A New Ultra-sensitive Analytical Technique for $^{14}C$ Analysis," Murnick et al., Analytical Chemistry, (2008), hereby incorporated by reference in its entirety.

In order to determine the proportion of fossil-fuel based carbon to modern carbon in biofuel products, a $\Delta^{14}C$ mass balance may be used:

$$\Delta^{14}C_{mixture} = F_{c,fossil}\Delta^{14}C_{petro} + (1-F_{c,fossil})\Delta^{14}C_{modern} \quad (1)$$

The $\Delta^{14}C$ nomenclature is the per mille (‰) deviation from the international $^{14}C$ standard, described in National Institute of Technology (NIST) Standard Reference Material 4990B "Oxalic Acid I", hereby incorporated by reference in its entirety. The $\Delta^{14}C_{mixture}$ is the measured $^{14}C$ content of the biofuel. The $\Delta^{14}C_{modern}$ is the measured dissolved inorganic carbon from the local environment, such as the atmosphere (for terrestrial plants/biofuel precursors) or water (for aquatic plants/biofuel precursors). For example, the $\Delta^{14}C_{modern}$ for dissolved inorganic carbon in seawater is approximately +50 per mille (‰). The $\Delta^{14}C_{fossil}$ value is approximately −1000‰, consistent with numerous measurements of petroleum endmembers in our laboratory and exhaust of engines run on fossil-fuel diesel (Reddy et al. 2008). Finally, $F_{C,fossil}$ is the mass fraction of the total mixture carbon that is derived from fossil-fuel $CO_2$.

Rearranging eq 1, $F_{C,fossil}$ can be expressed as:

$$F_{c,fossil} = (\Delta^{14}C_{mixture} - \Delta^{14}C_{modern})/(\Delta^{14}C_{fossil} - \Delta^{14}C_{modern}) \quad (2)$$

Eq 2 shows that the proportion of fossil carbon in the sample ($F_{C,fossil}$) can be determined.

Measuring the radiocarbon content of biofuels may provide many advantages. For example, a biofuel producer may use the measured radiocarbon content of a biofuel product to state the amount of carbon in the biofuel product that is renewable or from a fossil source. As another example, significant amounts of money may be traded on the assumptions around carbon uptake, which goes to regulations to credits, cap and trade, etc., and a robust and accurate method for determining fossil-fuel $CO_2$ uptake is desirable.

Moreover, measuring biofuel radiocarbon content provides a robust means to determine the amount of fossil-fuel-based carbon that has been incorporated into the final product, and may be used to determine the efficacy of carbon injection and capture techniques. For example, in the field of marine-biofuel generation, operators may decide to build their biofuel generation systems near fossil-fuel-based power plants in order to utilize the carbon dioxide emissions from the power plants for generating biofuel in their systems. The ability to measure and monitor the radiocarbon content of the resulting biofuel product may allow operators or designers to gauge the efficiency of fossil-fuel-based carbon ("fossil-carbon") uptake in their systems. Moreover, if the radiocarbon contents of the various inputs of a biofuel generation system can be measured, modifications to the aquatic biofuel generation system may be implemented in order to achieve a desired biofuel fossil-carbon content in the final biofuel product. These modifications, while also suitable for terrestrial biofuel generation systems, are particularly useful for aquatic biofuel generation systems, because the radiocarbon content of aquatic vegetation can be controlled by modifying the radiocarbon content of the water the vegetation is grown is, as described in "Radiocarbon Dating of Alkenones from Marine Sediments: II. Assessment of Carbon Process Blanks," Mollenhauer et al., Radiocarbon, vol. 47, no. 3, (2005), hereby incorporated by reference in its entirety. Carbon may be introduced to water by bubbling carbon-bearing gases through, and the amount of carbon dissolved in the water may be controlled by varying the rate at which carbon-bearing gases are bubbled through the water.

FIG. 1 depicts a system 100 for manufacturing biofuel, according to an illustrative embodiment of the invention. The system 100 includes several components: a growth system 102, a refinery 104, an analyzer 120, a computer 122, and an interface 124. Growth system 102 may be configured to grow one or more biofuel precursors or feedstocks. For example, in one embodiment, the growth system 102 may be configured to grow aquatic vegetation such as algae.

To support vegetation growth, the growth system 102 may be configured to receive feedstock such as carbon, water, and light via carbon input 106, water input 108, and light input 110. In some embodiments, carbon input 106 may be in the form of a gas containing inorganic, organic, and/or fossil-based carbon dioxide. In some embodiments, the carbon input 106 may be obtained from the ambient environment, such as the atmosphere. In other embodiments, carbon input 106 may be obtained from a source such as a fossil fuel facility, such as a coal or natural gas power plant, that outputs flue gas rich in carbon dioxide. In these embodiments, the flue gas from the fossil fuel plant may be used as the carbon input 106 directly, or may be purified before being supplied to the growth system 102. Flue gas purification may involve the scrubbing/removal of particular chemical species from the flue gas, such as sulfur-containing particles or soot/ash/particulates.

The water input 108 may provide water as growth medium for aquatic vegetation, or simply as water for terrestrial vegetation. In some embodiments, water input 108 may include seawater. For embodiments including aquatic vegetation, the growth system 102 may also be configured to output water 114 to maintain an open-loop flow system and to flush wastes from the growth system 102. The water output 114 may be filtered and recirculated into the growth system 102 as water input 108, or may be discarded into the ambient environment. The light input 110 may be natural light (e.g., sunlight) or artificial light.

In some embodiments, there may be material leakage/transfer 112 between the growth system 102 and the ambient environment. For example, carbon or moisture may be transferred to or from the ambient atmosphere to the growth system 102. In some cases, this may be desirable (e.g., open pond growth systems). However, in other cases, leakage 112 may be undesirable or unexpected, and characterization of the leakage 112 may be needed to fully characterize the inputs/outputs of the growth system 102.

The growth system 102 may output an intermediate biofuel product 116, which may then be used as input into a refinery 104. For example, vegetation grown in the growth system 102 may be harvested and used as feedstock for the refinery 104. In other embodiments, some processing may be performed on the harvested vegetation within the growth system 102 to produce the intermediate biofuel product 116. For example, the harvested vegetation may be digested, fermented, and/or converted within the growth system 102 into an unpurified alcohol product. The refinery 104 may then take the intermediate biofuel product 116, whether it is raw, harvested vegetation or some form of processed vegetation, and convert it into a final biofuel product 118, such as ethanol, biodiesel, or biogas.

In some embodiments, radiocarbon content measurements may be taken of one or more of the various inputs, outputs, and stages of the system 100, in order to determine a radiocarbon content balance for the system and to determine the amount of carbon input 106 incorporated into the intermediate biofuel product 116 and/or the final biofuel product 118. For example, analyzer 120 may be configured to take radiocarbon measurements of the intermediate biofuel product 116 and/or the final biofuel product 118 to determine the amount of fossil carbon in the biofuel products. In some embodiments, the analyzer 120 may be configured to measure radiocarbon content in any input, output, or stage of the growth system 102. For example, in some embodiments, the analyzer 120 may also take radiocarbon measurements of the carbon input 106, the water input 108 and output 114, and the leakage 112 in order to determine a radiocarbon content balance for the growth system 102. Optionally, radiocarbon content measurements may be taken of the various components within the growth system 102 and/or the refinery 104, in order to determine carbon content flow within the growth system 102 and/or the refinery 104. In certain embodiments, the radiocarbon content of any carbon-containing moiety or compound input or present in growth system 102 and/or the refinery 104 may be measured. For example, the dissolved inorganic carbon, dissolved organic carbon, and/or the algal biomass in the water input 108 and/or the water present in the growth system 102. In certain embodiments, the radiocarbon content of any raw lipid extract of the algae/vegetation (which may be included in intermediate biofuel product 116), the final biofuel product 118, and/or the atmosphere in any enclosed facility that contains the growth system 102 and/or the refinery 104 may be measured. The measured radiocarbon contents and carbon balances may then be used to modify the various inputs, the growth system 102, and/or the refinery 104, in order to control the radiocarbon content of the intermediate biofuel product 116 and/or the final biofuel product 118. For example, a computer 122 may receive measured radiocarbon content data from the analyzer 120 and adjust various parameters of the inputs, the growth system 102, and/or the refinery 104 based on the received radiocarbon content data.

Computer 122 may store information related to the measured radiocarbon content data and/or data related to the various inputs and components of the growth system 102. Computer 122 may also communicate this information to other computers (not shown), for example via a network (also not shown) such as a local are network, wide area network, or the Internet.

Computer 122 may include a central processing unit (CPU), a memory, and an interconnect bus. The CPU may include a single microprocessor or a plurality of microprocessors for configuring computer 122 as a multi-processor system. The memory may include a main memory and a read only memory. The computer 122 may also include a mass storage device having, for example, various disk drives, tape drives, FLASH drives, etc. The main memory also includes dynamic random access memory (DRAM) and high-speed cache memory. In operation, the main memory stores at least portions of instructions and data for execution by the CPU.

The mass storage may include one or more magnetic disk or tape drives or optical disk drives, for storing data and instructions for use by the CPU. In certain embodiments, at least one component of the mass storage system, preferably in the form of a disk drive or tape drive, may store a database.

The mass storage system may also include one or more drives for various portable media, such as a floppy disk, a compact disc read only memory (CD-ROM), DVD, or an integrated circuit non-volatile memory adapter (i.e. PC-MCIA adapter) to input and output data and code to and from the computer 122.

The computer 122 may also include an interface 124 for communications. The interface 124 may comprise one or more of a modem, a network card, serial port, bus adapter, or any other suitable data communications mechanism. Computer 122 may also communicate with other computers via, for example, optical, wired, or wireless methods (e.g., via satellite or cellular network). The interface 124 may also include user interfaces, such as displays, keyboards, mice, or any other means for communicating with a human user or operator.

In certain embodiments, the computer 122 may include sensors for sensing various characteristics associated with the inputs, outputs, and stages of the system 100, such as temperature, and solute concentration, and may also include actuators for controlling parameters associated with the inputs, outputs, and stages of the system 100. For example, the computer 122 may be configured to control flow rates of the various inputs and outputs, the amount of light that is transmitted into the growth system 102, and/or the amount of intermediate biofuel product 116 and/or final biofuel product 118 that is output by the growth system 102 and/or the refinery 104.

Figure 2:
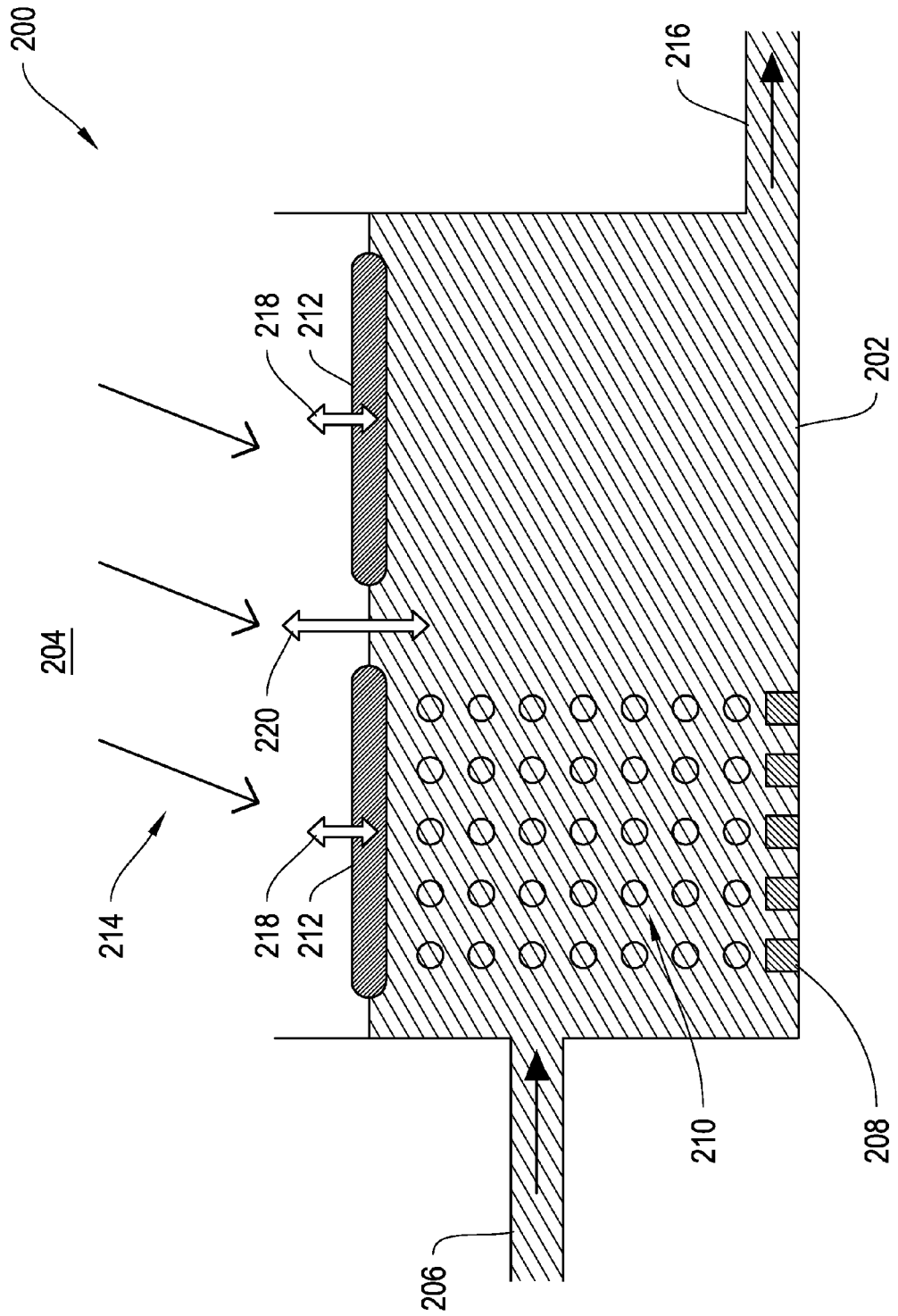
FIG. 2 depicts a growth system for biofuel manufacture open to ambient atmosphere, according to an illustrative embodiment of the invention.

FIG. 2 depicts a growth system 200 for biofuel manufacture open to ambient atmosphere, according to an illustrative embodiment of the invention. In some embodiments, growth system 200 is configured for the growth of aquatic vegetation 212 (e.g., algae) with exposure to the ambient atmosphere 204. The growth system 200 may include one or more bioreactors and/or holding vessel(s) 202 at least partially filled with water for aquatic vegetation growth. The water in the holding vessel 202 may be selected based on the type of aquatic vegetation to be grown. For example, if freshwater vegetation is to be grown, the holding vessel 202 may contain fresh water. Likewise, if saltwater vegetation is to be grown, the holding vessel 202 may contain saltwater or seawater. The holding vessels may include, for example, holding ponds, tanks, bags, and/or other containers configured to hold liquid and allow the transmission of light 214, which may be natural (e.g., sunlight) or artificial. Optionally, the growth system 200 may be located near or within a body of water, wherein at least part of the body of water comprises the holding vessel(s). In some embodiments, the holding vessel 202 may be physically open to the ambient environment, allowing gas exchange between the liquid within the holding vessel 202 and the ambient environment 204.

The holding vessel 202 may be configured with a water input port 206, via which water is added to or pumped into the holding vessel. In some embodiments, the holding vessel 202 may also include a water output port 216, via which water may be removed from the holding vessel. In some embodiments, the growth system 200 may be configured for vegetation growth in a substantially static environment, in which the liquid within the holding vessel 202 is disturbed as little as possible. In these embodiments, water may be added and/or removed from the holding vessel 202 only when water parameters exceed or drop below some desired threshold. For example, more water may be added if the water in the holding vessel 202 drops below a certain level, or if solute concentrations within the water rise or decrease to undesirable levels. In other embodiments, the growth system 200 may be configured for vegetation growth in a dynamic flow environment. In these embodiments, water may be added (and removed) constantly or periodically in order to create a water flow within the holding vessel 202. In some embodiments, the water input port 206 and/or the water output port 216 may include one or more filtration devices (not shown) to prevent the movement of vegetation 212 into the input port 206 and/or the output port 216. In other embodiments, movement of vegetation 212 between different holding vessels may be desirable, and in these embodiments, the input port 206 and/or the output port 216 may be sized to allow vegetation 212 to pass through.

The growth system 200 may also be configured with means for adding carbon-bearing gases into the holding vessel 202. In some embodiments, the growth system 200 may include one or more gas release devices 208, such as gas bubblers, for releasing carbon-bearing gases 210 into the water within holding vessel 202. The gas release devices 208 may be linked to a carbon gas source, such as the unprocessed or processed flue gas emissions from a fossil-fuel power plant, and may be configured in a number of ways.

In some embodiments, the gas release device(s) 208 may comprise one or more gas-carrying pipes or tubes, each with one or more gas outlets configured to release gas 210 in one or more locations within the holding vessel 202. The configuration of the gas release devices 208 may be guided by the measured radiocarbon content in the vegetation 212, intermediate biofuel product 116 (FIG. 1), and/or the final biofuel product 118 (FIG. 1), and a desired final product radiocarbon content. In some embodiments, configuring the gas release devices 208 to release fossil-carbon-containing gas 210 from a plurality of locations within the holding vessel 202 instead of releasing gas 210 from only one location may decrease the measured final product radiocarbon content, because the gas distribution in the holding vessel 202 may become more uniform, and the vegetation 212 may absorb more of the released gas 210. Similarly, configuring the gas-release devices 208 to provide higher gas release rates may also decrease the final product radiocarbon content, because the resulting higher concentration of fossil-carbon may result in higher uptake of fossil-carbon by the vegetation 212. In certain embodiments, these parameters may be varied dynamically, such as according to time of day, time of season, incident light, ambient temperature, water temperature, water solute concentrations/gas concentrations, or any other relevant parameter. In other embodiments, other parameters of gas release devices 208 that may be configured include pipe/tube diameter, gas outlet positioning, the static or dynamic placement of device components, etc.

In other embodiments, the configuration of the gas release devices 208 may be guided by the measured radiocarbon content and/or carbon content in other inputs and stages of the growth system 200, such as the water input 206 and output 216, water-atmosphere carbon transfer 220, vegetation-atmosphere carbon transfer 218, and other components of the growth system 200. For example, if the radiocarbon content of the water input 206 is measured to be higher than a particular threshold, then the gas release devices 208 may be configured to release more carbon-bearing gas 210 into the system to offset the higher radiocarbon content of the water input. As another example, if the water-atmosphere carbon transfer 220 and/or the vegetation-atmosphere carbon transfer 218 is measured to be higher than one or more particular thresholds, then the gas release devices 208 may be configured to release less carbon-bearing gas 210 in order to reduce carbon loss to the atmosphere.

In certain embodiments, parameters of other elements of the growth system 200, such as size, shape, and composition of the holding vessel 202, the type of aquatic vegetation 212, the type and composition of the water, the amount of light allowed into the growth system 200, etc., may be modified to alter the measured final product radiocarbon content. Similarly, other components may be added to the system to control measured final product radiocarbon content, such as water mixers/agitators, water/atmospheric heaters, water/atmospheric sensors, etc.

In some embodiments, the growth system 200 may include one or more radiocarbon sensors or sample collectors (not shown) coupled to the various inputs and components of the system, in order to determine radiocarbon content. For example, there may be sensors or sample collectors disposed near or within the water input port 206 and/or the water output port 216 for the determination of radiocarbon content of the incoming and/or outgoing water. Similarly, there may be sensors/sample collectors disposed at various locations within the holding vessel 202 for the determination of water radiocarbon content at the different locations within the holding vessel. In some embodiments, sensors/sample collectors may be disposed around the holding vessel 202 for the determination of radiocarbon content in the ambient atmosphere 204. There may also be sensors/sample collectors disposed to measure the radiocarbon content of the incoming carbon-bearing gases to be released by the gas release devices 208. Using the collected radiocarbon data, a carbon balance model may be determined for the growth system 200, which may indicate how carbon, fossil-fuel-based or otherwise, is entering or leaving the system. Using this model and data, modifications may be made to the growth system 200 in order to change the radiocarbon content of the vegetation 218.

Figure 3:
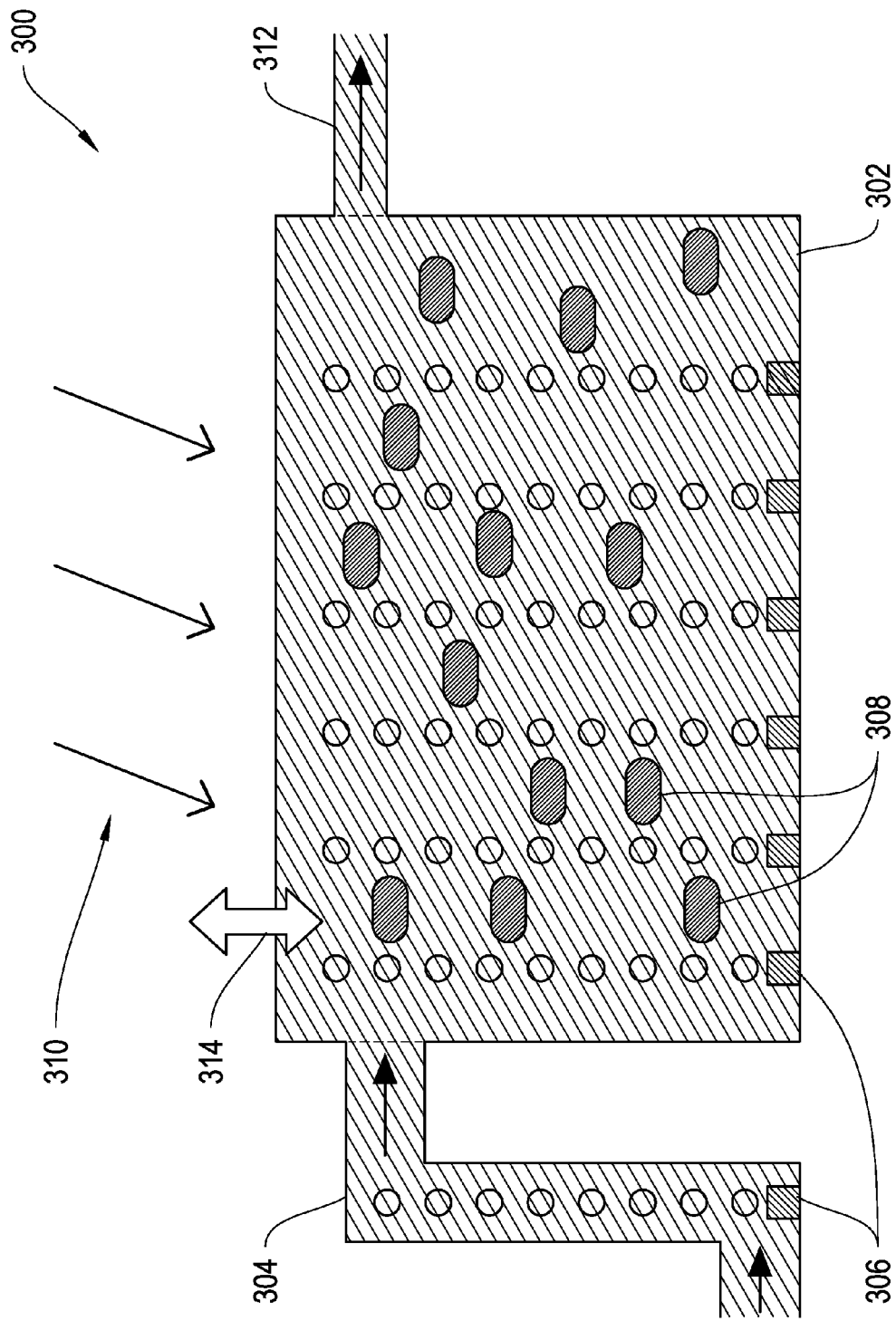
FIG. 3 depicts a growth system for biofuel manufacture closed to ambient atmosphere, according to an illustrative embodiment of the invention.

FIG. 3 depicts a growth system 300 for biofuel manufacture that is closed to ambient atmosphere, according to an illustrative embodiment of the invention. While the growth system 300 is similar to the growth system 200 depicted in FIG. 2, in contrast to the growth system 200, the bioreactor/holding vessel 302 of growth system 300 is configured to prevent exposure of its contents to ambient atmosphere, while allowing the transmission of light 310 (natural and/or artificial) into the holding vessel. By limiting the exposure of the contents of the bioreactor/holding vessel 302 to ambient atmosphere and its load of radiocarbon (corresponding to modern/contemporary levels of radiocarbon), the amount/proportion of fossil carbon in the growth system 300 may be increased, which may result in higher fossil carbon uptake by vegetation in growth system 300 as compared to vegetation in growth system 200, which is open to the ambient atmosphere. To achieve this, the holding vessel 302 may be sealed against the ambient environment, with suitable input and output ports for water input (304), water output (312), and gas release devices (306). The holding vessel 302 may also be at least partially transparent to allow for natural or artificial light 310 to be transmitted into its interior, and also to allow for inspection of its contents. In some embodiments, the holding vessel 302 may also include internal lighting sources (not shown), for increased distribution of light in its interior. Gas release devices 306 may be configured to operate in a fashion similar to gas release devices 208 (FIG. 2). As with the growth system 200 described in FIG. 2, radiocarbon sensors/collection devices (not shown) may be disposed near various inputs, outputs, and components of the holding vessel 302 in order to measure radiocarbon content.

Although the holding vessel 302 may be configured to prevent exposure of its contents to ambient atmosphere, in many circumstances undesired leakage/transfer of material into and out of the holding vessel 302 may occur, indicated by material leakage/transfer 314. In some embodiments, additional radiocarbon sensors/collection devices may be disposed to detect leaks into and out of the growth system 300/ holding vessel 302. Optionally, instead of having sensors specifically for detecting leakage, the leakage/transfer 314 may be indirectly determined via a carbon balance model for the growth system 300 built from radiocarbon content data collected by sensors within the system. As with growth system 200 described in FIG. 2, the carbon balance model for the growth system 300 may be used to determine modifications to the system in order to change the radiocarbon content of the vegetation 308.

Figure 4:
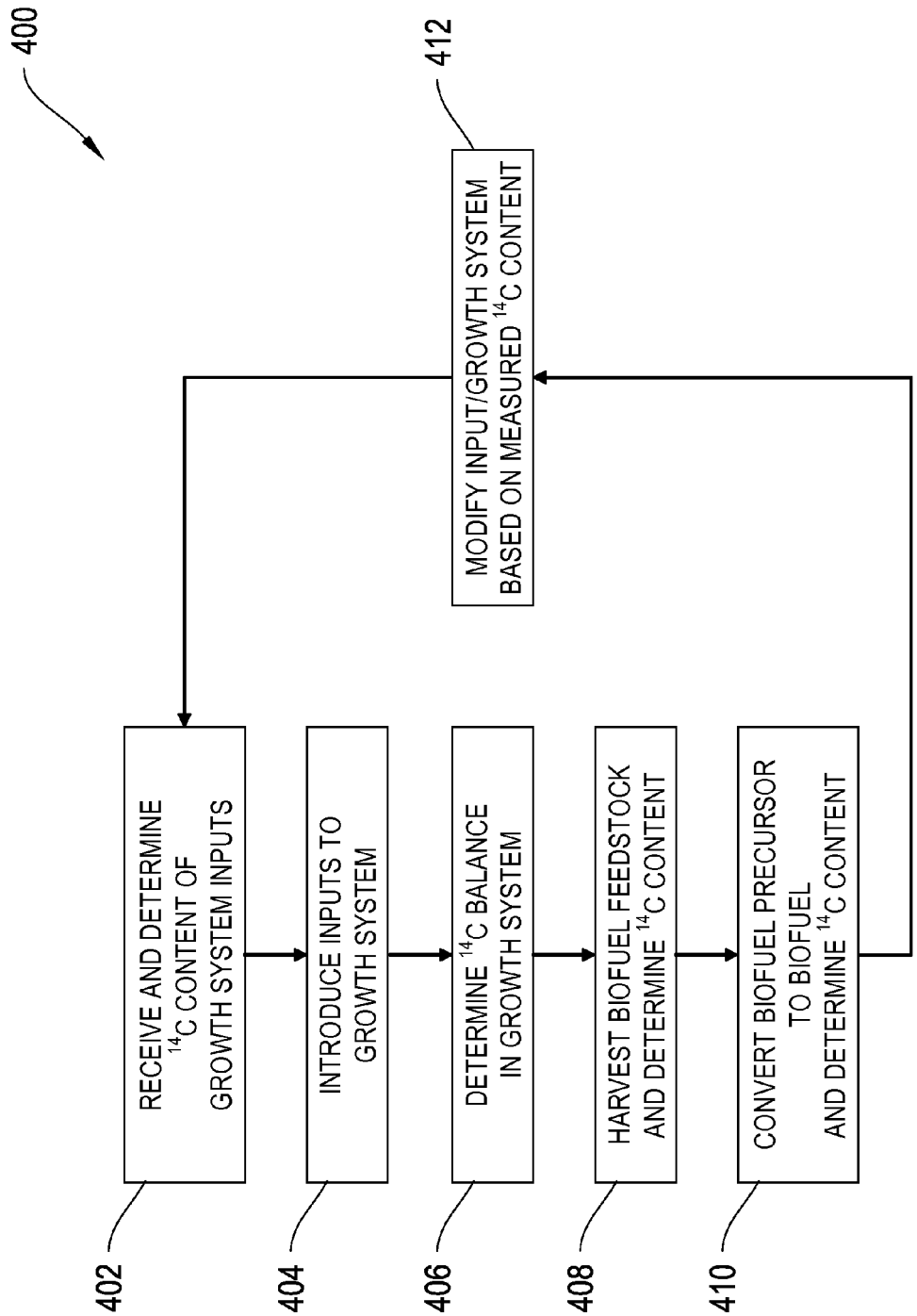
FIG. 4 is a flowchart depicting a process for controlling the fossil carbon content of manufactured biofuel based on radiocarbon measurements, according to an illustrative embodiment of the invention.

FIG. 4 is a flowchart depicting a process loop 400 for controlling the fossil carbon content of manufactured biofuel based on radiocarbon measurements, according to an illustrative embodiment of the invention. In certain embodiments, the radiocarbon measurements may be used to monitor the performance of the overall system, so that any unexpected or undesirable changes in radiocarbon content may be detected. In some embodiment, a biofuel producer may use the measured radiocarbon content of the final biofuel product to confidently state the amount of carbon in the biofuel product that is renewable or from a fossil source.

In step 402 of process loop 400, growth system inputs, such as water or carbon-bearing gases, are received, and their radiocarbon contents are determined. The growth system inputs are then introduced to the growth system in step 404 to grow biofuel feedstock/vegetation. During vegetation growth, measurements of radiocarbon content within the growth system are taken in step 406, and a radiocarbon balance/model for the growth system is generated and/or updated. In step 408, biofuel feedstock/vegetation is harvested, and its radiocarbon content is determined. In step 410, the biofuel feedstock/vegetation is converted into biofuel, and one or more radiocarbon content measurements are taken during the conversion process. The measured radiocarbon content data collected in these steps, as well as the radiocarbon balance/model generated and updated in step 406, are then used in step 412 to effect modifications to the inputs and/or the growth system in order to achieve a desired biofuel/feedstock radiocarbon level, and then process 400 begins again at step 402. In some embodiments, the modifications to the inputs and/or the growth system may be performed at any time, in response to radiocarbon content data collected during any of the steps. For example, in certain embodiments, instead of only modifying inputs and the growth system after determining the radiocarbon content of the final biofuel product, the system and/or inputs may be modified if the radiocarbon balance/model generated and/or updated in step 406 indicates an abnormality in the growth system (e.g., too much radiocarbon or too little radiocarbon).

Various modifications may be made in step 412. In some embodiments, the release rate and release characteristics of carbon-bearing gases may be modified. For example, the gas release devices 208/306 (FIGS. 2-3) may be modified to release carbon-bearing gases at different rates. If the radiocarbon content in the biofuel feedstock/vegetation is to be decreased, gas release devices may be configured to release fossil carbon-bearing gases faster. If a particular region of a holding vessel has a higher radiocarbon content than desired, gas release devices that serve that region may be configured to release fossil carbon-bearing gases faster.

In other embodiments, data other than radiocarbon data may be collected during any of the steps in process 400, such as water solute content, quantity of light exposure, or amount of material transfer/leakage, and the modifications of the system performed in step 412 may be determined based on these other data. For example, if the pH of the water in the growth system is lower than a particular threshold, the system may be modified to increase the water pH, by decreasing the amount of carbon dioxide released into the water or by adding a basic agent to the water.

Variations, modifications, and other implementations of what is described may be employed without departing from the spirit and scope of the invention. More specifically, any of the method, system, and device features described above or incorporated by reference may be combined with any other suitable method, system or device features disclosed herein or incorporated by reference, and is within the scope of the contemplated inventions. The systems and methods may be embodied in other specific forms without departing from the spirit or essential characteristics thereof. The foregoing embodiments are therefore to be considered in all respects illustrative, rather than limiting of the invention. The teachings of all references cited herein are hereby incorporated by reference in their entirety.

The invention claimed is:

1. A method of growing photosynthetic organisms with controlled fossil carbon content for generating a biofuel product, comprising:
   disposing the photosynthetic organisms within a biofuel growth system configured to receive one or more feedstocks and generate a biofuel product;
   adding the one or more feedstocks to the biofuel growth system;
   measuring the fossil carbon content of the biofuel product; and regulating at least one of a parameter of the one or more feedstocks and a parameter of the growth system based on the measured fossil carbon content of the biofuel product.

2. The method of claim 1, wherein the measurement of fossil carbon content is based at least in part on radiocarbon analysis.

3. The method of claim 1, further comprising at least one of measuring the fossil carbon content of at least one of the one or more feedstocks and measuring the fossil carbon content within the biofuel growth system, and wherein the regulation of at least one of a parameter of the one or more feedstocks and a parameter of the growth system is further based on at least one of the measured fossil carbon content of the one or more feedstocks and the measured fossil carbon content within the biofuel growth system.

4. The method of claim 1, wherein the biofuel product is at least one of digested, fermented, and converted vegetation.

5. The method of claim 1, further comprising refining the biofuel product.

6. The method of claim 1, wherein the one or more feedstocks includes a carbon-bearing gas, and wherein regulating at least one of a parameter of the one or more feedstocks and a parameter of the growth system includes adjusting at least one parameter associated with the addition of the carbon-bearing gas to the growth system.

7. The method of claim 6, wherein the at least one parameter includes at least one of a carbon-bearing gas addition rate, a carbon-bearing gas addition location, a quantity of carbon-bearing gas, a type of carbon-bearing gas, and a source of carbon-bearing gas.

8. The method of claim 6, wherein the carbon-bearing gas is a flue gas resulting from the combustion of a fossil fuel.

9. The method of claim 8, wherein the flue gas is received from a fossil fuel power plant.

10. The method of claim 1, wherein the photosynthetic organisms include algae.

* * * * *